United States Patent
Huber et al.

(10) Patent No.: US 11,360,070 B2
(45) Date of Patent: Jun. 14, 2022

(54) METHOD FOR DETERMINING THE METHANE INDEX OF A HYDROCARBON-CONTAINING COMBUSTION GAS MIXTURE

(71) Applicant: Endress+Hauser Flowtec AG, Reinach (CH)

(72) Inventors: Christof Huber, Bern (CH); Patrick Reith, Basel (CH); Anastasios Badarlis, Birsfelden (CH)

(73) Assignee: ENDRESS+HAUSER FLOWTEC AG, Reinach (CH)

( * ) Notice: Subject to any disclaimer, the term of this patent is extended or adjusted under 35 U.S.C. 154(b) by 205 days.

(21) Appl. No.: 16/499,517

(22) PCT Filed: Feb. 15, 2018

(86) PCT No.: PCT/EP2018/053826
§ 371 (c)(1),
(2) Date: Sep. 30, 2019

(87) PCT Pub. No.: WO2018/177651
PCT Pub. Date: Oct. 4, 2018

(65) Prior Publication Data
US 2020/0041479 A1 Feb. 6, 2020

(30) Foreign Application Priority Data
Mar. 30, 2017 (DE) .................... 10 2017 106 904.6

(51) Int. Cl.
*G01N 33/22* (2006.01)
*F02M 37/00* (2006.01)
(Continued)

(52) U.S. Cl.
CPC ....... *G01N 33/225* (2013.01); *F02M 37/0047* (2013.01); *G01N 9/36* (2013.01); *G01N 11/16* (2013.01)

(58) Field of Classification Search
CPC ........ G01N 33/225; G01N 11/16; G01N 9/36; F02M 37/0047; Y02T 10/30;
(Continued)

(56) References Cited

U.S. PATENT DOCUMENTS

| 2002/0124630 A1 | 9/2002 | Jaeschke et al. |
| 2004/0195531 A1 | 10/2004 | Rahmouni et al. |
| 2018/0038811 A1* | 2/2018 | Hornung .............. G01N 25/005 |

FOREIGN PATENT DOCUMENTS

| CN | 1549927 A | 11/2004 |
| CN | 101571500 A | 11/2009 |

(Continued)

OTHER PUBLICATIONS

Goodwin, A. R. H., et al. "A vibrating plate fabricated by the methods of microelectromechanical systems (MEMS) for the simultaneous measurement of density and viscosity: Results for argon at temperatures between 323 and 423K at pressures up to 68 MPa." International Journal of Thermophysics 27.6 (Year: 2006).*

*Primary Examiner* — Herbert K Roberts
*Assistant Examiner* — Fatemeh Esfandiari Nia
(74) *Attorney, Agent, or Firm* — Christopher R. Powers; Endress+Hauser (USA) Holding Inc.

(57) ABSTRACT

The present disclosure relates to a method for determining the methane index of a hydrocarbon-containing combustion gas mixture which has natural gas or biogas, having the steps: flowing the gas mixture through a measuring assembly; determining a first value of a first measurement variable related to a viscosity of the gas mixture; determining a second value of a second measurement variable related to a density of the gas mixture; determining a pressure value of (Continued)

the gas mixture, said pressure value belonging to the first value and the second value; determining a temperature value of the gas mixture, said temperature value belonging to the first value and the second value; and determining the methane index as a function of the first value, the second value, the pressure value, and the temperature value.

12 Claims, 3 Drawing Sheets

(51) Int. Cl.
    *G01N 11/16*     (2006.01)
    *G01N 9/36*     (2006.01)

(58) Field of Classification Search
    CPC ..... F02D 2200/0602; F02D 2200/0612; F02D 19/029; F02D 41/0027
    See application file for complete search history.

(56) References Cited

FOREIGN PATENT DOCUMENTS

| | | | | |
|---|---|---|---|---|
| CN | 101910837 A | 12/2010 | | |
| CN | 103038634 B | 1/2016 | | |
| CN | 105606786 A | 5/2016 | | |
| CN | 105765352 A | 7/2016 | | |
| DE | 102014115566 A1 * | 5/2015 | ............. | G01F 1/692 |
| DE | 102014115566 A1 | 5/2015 | | |
| DE | 102014106729 A1 | 11/2015 | | |
| DE | 102014119212 A1 | 6/2016 | | |
| DE | 102015117468 A1 | 4/2017 | | |
| EP | 2574918 A1 | 4/2013 | | |
| EP | 2806271 A1 | 11/2014 | | |
| WO | 2015075278 A1 | 5/2015 | | |

* cited by examiner

METHOD FOR DETERMINING THE METHANE INDEX OF A HYDROCARBON-CONTAINING COMBUSTION GAS MIXTURE

CROSS-REFERENCE TO RELATED APPLICATIONS

The present application is related to and claims the priority benefit of German Patent Application No. 10 2017 106 904.6, filed on Mar. 30, 2017, and International Patent Application No. PCT/EP2018/053826 filed on Feb. 15, 2018, the entire contents of which are incorporated herein by reference.

TECHNICAL FIELD

The present invention relates to a method for determining the methane index of a hydrocarbon-containing combustion gas mixture. Typical combustion gas mixtures are, for example, natural gas or biogas.

BACKGROUND

Natural gas is a fossil fuel. It has a storage-facility-dependent composition. The principal constituent of natural gas is methane, with a molar fraction of, for example, 75% to 99%. Natural gas frequently also contains larger fractions of ethane (1% to 15%), propane (1% to 10%), butane, and ethene. Further minor constituents are hydrogen sulfide, nitrogen, carbon dioxide, and water vapor.

Biogas is a combustible gas mixture of varying composition which is produced by fermentation of biomass of any type. In the crude state, it contains, in particular, methane (up to 60%) and carbon dioxide as main components. Also included are nitrogen, oxygen, hydrogen sulfide, water vapor, and ammonia. Hydrogen sulfide and ammonia must be removed before burning or before feeding into the natural gas network.

The still unpublished patent application DE 102015117468.5 discloses a method for the method for determining the Wobbe index or the calorific value and the inert gas fraction of gas mixtures, which, in particular, include natural gas or biogas, on the basis of the viscosity and the density or sound velocity.

However, the gas network is increasingly used as an energy store for alternatively generated gas from "Power to Gas" ($H_2$) and "Biogas" ($CH_4+CO_2$) enriched with liquid petroleum gas ($C_2H_6+C_3H_8$). This significantly changes the gas composition in the network. The gas quality at the consumer fluctuates greatly, and rapid changes can occur. The hydrogen fraction can be up to 20%. The Wobbe index is suitable only to a limited extent as a measure for good burner control, because $H_2$ behaves differently than natural gas.

The still unpublished patent application DE 102016121226.1 discloses a method for determining the calorific value of a hydrogen-containing combustion gas mixture.

If a combustion gas mixture is to be used for operating an internal combustion engine, the knock resistance of the combustion gas mixture is important, in addition to the calorific value. The methane index provides a description of knock behavior of a combustion gas mixture in an internal combustion engine, wherein a combustion gas mixture having a methane index of zero has the same knock resistance as pure hydrogen, and a mixture having a methane index of 100 has the same knock resistance as pure methane. Details regarding the methane index are described, for example, in "BHKW and methane index, influence of the gas quality on engine operation" of the Association for the Efficient and Environmentally Friendly Use of Energy or in "Algorithm for methane number determination for natural gasses," ISBN 87-7795-125-5, by Paw Andersen.

The methane index $MZ'$ of a combustion gas mixture can accordingly be calculated experimentally using a test engine or as a weighted mean value of the methane indices $MZ_i$ of component groups of the combustion gas mixture.

$$MZ' = \frac{1}{100}\sum y_i MZ_i$$

However, the above calculation method requires knowledge of the methane indices $MZ_i$ of the component groups and the proportion $y_i$ thereof in the combustion gas mixture. Moreover, the methane indices of the component groups must not differ too drastically from one another. Otherwise, the component groups must be newly composed. This requires a lengthy procedure including complex measurements for determining the fractions of the component groups, in particular, when this results in a determination of the fractions of the individual components.

SUMMARY

It is therefore the aim of the present invention to provide a simpler method for determining the methane index of a hydrocarbon-containing combustion gas mixture. The aim is achieved according to the invention by the method according to independent claim 1.

The method according to the invention for determining the methane index of a hydrocarbon-containing combustion gas mixture, which, in particular, has natural gas or biogas, comprises:

allowing the combustion gas mixture to flow through a measuring assembly;

determining a first measurement value of a first measurement variable dependent upon the viscosity of the flowing combustion gas mixture;

determining a second measurement value of a second measurement variable dependent upon the density of the flowing combustion gas mixture;

determining a pressure measurement value, belonging to the first measurement value and the second measurement value, of the flowing combustion gas mixture; and determining a temperature measurement value, belonging to the first measurement value and the second measurement value, of the flowing combustion gas mixture; and determining the methane index as a function of the first measurement value, the second measurement value, the pressure measurement value, and the temperature measurement value.

The method according to the invention thus enables a simple and robust determination of the methane index on the basis of few measurement variables, without having to precisely know the exact fractions of individual components or component groups. The different correlations of density and viscosity with the fractions of the component groups defining the methane index enable, as an intermediate step, a sufficiently precise determination of the average molar mass of hydrocarbon compounds and the fraction of foreign components, as will be explained in more detail below. The methane index can be determined from these variables by correlation calculation. Although the procedure using the described intermediate steps is more intuitive to follow because the methane index is assigned to the cited material properties of the combustion gas mixture, the steps can be dispensed with, and the methane index can be directly assigned to the observed viscosity- and density-dependent measurement variables on the basis of correlation calculations.

The measurement values of pressure and temperature are used, in particular, to correct their influence on the first measurement value of the first measurement variable and the second measurement value of the second measurement variable—for example, by tracing the first measurement value and the second measurement value back to reference conditions, in particular, standard conditions.

In one embodiment of the invention, the first measurement variable characterizes a damping of oscillations of an oscillator exposed to the combustion gas mixture, or describes a pressure drop across a throttle. The first measurement variable can, for example, be a resonance width of a forced oscillation, a correlation between a phase angle between an excitation signal and an oscillation signal of the oscillator on the one hand, and the ratio between the excitation frequency and the natural frequency of the oscillator on the other, as well as the ratio between the oscillation amplitude and the excitation signal amplitude.

In one embodiment of the invention, the second measurement variable comprises a natural frequency of an oscillator exposed to the combustion gas mixture or the sound velocity of the combustion gas mixture.

In one embodiment of the invention, the method according to the invention furthermore comprises determining a third measurement value characterizing the thermal conductivity of the combustion gas mixture, wherein the third measurement value is likewise considered in the ascertainment of the methane index. The third measurement value is used, in particular, to determine the hydrogen content in the combustion gas mixture.

In one embodiment of the method according to the invention for determining the methane index of a hydrocarbon-containing combustion gas mixture, which, in particular, has natural gas or biogas, it comprises the following steps:

allowing the combustion gas mixture to flow through a measuring assembly;

determining a viscosity measurement value of the flowing combustion gas mixture;

determining a density or sound velocity measurement value of the flowing combustion gas mixture;

determining a value for the average molar mass of the hydrocarbons contained in the combustion gas mixture as a function of at least the viscosity measurement value and the density or sound velocity measurement value;

determining the methane index as a function of the value for the average molar mass of the hydrocarbon compounds contained in the combustion gas mixture.

In one embodiment of the invention, the determination of the value for the average molar mass of the hydrocarbon compounds contained in the combustion gas mixture comprises:

ascertaining a value for the average molar mass of the flowing combustion gas mixture as a function of the density or sound velocity measurement value of the flowing combustion gas mixture; and ascertaining a fraction of at least one foreign component in the combustion gas mixture, wherein the foreign component is free of hydrocarbon compounds;

ascertaining the value for the average molar mass of the hydrocarbon compounds contained in the combustion gas mixture as the average molar mass of the combustion gas mixture adjusted for the at least one foreign component, as a function of the ascertained value for the average molar mass of the flowing combustion gas mixture and the fraction of the at least one foreign component in the flowing combustion gas mixture.

In one embodiment of the invention, the at least one foreign component comprises inert gases contained in the combustion gas mixture, in particular, carbon dioxide and nitrogen.

In one embodiment of the invention, the determination of the inert gas fraction in the flowing combustion gas mixture comprises the following steps:

determining a first value of a variable characterizing the energy content of the combustion gas mixture as a function of the viscosity measurement value;

determining a second value of the variable characterizing the energy content of the combustion gas mixture as a function of the density or sound velocity measurement value of the flowing combustion gas mixture and independently of the viscosity measurement value; and determining the value for the inert gas fraction of the flowing combustion gas mixture as a function of a deviation between the first value and the second value of the variable characterizing the energy content of the combustion gas mixture.

In one embodiment of the invention, the second variable characterizing the energy content is the Wobbe index or the calorific value of the flowing combustion gas mixture.

In one embodiment of the invention, the at least one foreign component comprises the molecular hydrogen contained in the combustion gas mixture.

In one embodiment of the invention, the fraction of the molecular hydrogen is determined on the basis of a measurement of the thermal conductivity of the combustion gas mixture.

In one embodiment of the invention, the hydrogen fraction $X_{H2}$ is calculated as a function of the standard thermal conductivity of the molar mass or of the density and the (standard) viscosity.

In one embodiment of the invention, the fraction of the molecular hydrogen in the flowing combustion gas mixture is determined, wherein the average molar mass of the combustion gas mixture adjusted for the molecular hydrogen is determined as a function of the ascertained value for the average molar mass of the flowing combustion gas mixture and the fraction of the molecular hydrogen in the flowing combustion gas mixture, wherein the inert gas fraction in the combustion gas mixture adjusted for the molecular hydrogen is determined, wherein the average molar mass of the hydrocarbon compounds contained in the combustion gas mixture as a function of the average molar mass of the combustion gas mixture adjusted for the molecular hydrogen is determined as a function of the ascertained value for the average molar mass of the combustion gas mixture adjusted for the molecular hydrogen and the inert gas fraction in the combustion gas mixture adjusted for the molecular hydrogen; and wherein the methane index of the hydrocarbon compounds contained in the combustion gas mixture is determined on the basis of the ascertained value for the average molar mass of the hydrocarbon compounds contained in the combustion gas mixture.

In one embodiment of the invention, the methane index of the flowing combustion gas mixture is determined on the basis of the ascertained value for the methane index of the hydrocarbon compounds contained in the combustion gas mixture.

According to one embodiment of the invention, the ascertained values of the methane index are provided for controlling an internal combustion engine, a mixing device for combustion gas mixtures, or another data processing device.

The method according to the invention is based, in particular, upon the statistical analysis of the physical properties of several thousand combustion gas mixtures as a function of the composition thereof. The composition was determined by gas chromatography. For the ascertained compositions, the physical properties of the gas mixtures were ascertained by calculation at different pressure and temperature values. In like manner, the physical properties of some pure gases were calculated. For the ascertainment of the physical properties by calculation, a program of the NIST was used, viz., "Reference Fluid Thermodynamic and Transport Properties Database," abbreviated as REFPROP, version 9.1, which can be accessed at the address www.nist-.gov/srd/nist23.cf.

In particular, the PPDS (physical property data software) offered by NEL, a TÜV &id company, is suitable for calculating the thermal conductivity of arbitrary combustible gas compositions. Information on this is available from www.tuvnel.com/site2/subpage/software_solutions_ppds. Methane indices for combustion gas mixtures can be calculated according to the so-called AVL method using software from EON. For details, visit www.eon.com/en/businessareas/technical-services/gascalc-software/gascalc-module.htm.

An experimental determination of the physical quantities is also possible, but requires a greater effort.

The physical quantities ascertainable by calculation include:
  density: $\rho(T,p)$, using NISTrefprop or PPDS
  molar mass, using NISTrefprop or PPDS
  sound velocity SOS, using NISTrefprop or PPDS
  dynamic viscosity: $\eta(T,p)$, using NISTrefprop or PPDS
  calorific value: CV, using NISTrefprop or PPDS
  Wobbe index: $WI=CV/\sqrt{SG}$, using NISTrefprop or PPDS
  thermal conductivity $\lambda(T,p)$, using PPDS
  methane index, using www.eon.com/en/business-areas/technical-services/gascalc-software/gascalc-module.html.

The method according to the invention was developed on the basis of the above data.

The device according to the invention is used to determine at least the methane index of a hydrocarbon-containing gas mixture using the method according to the invention, wherein the device comprises:
  a measuring assembly through which the gas mixture can flow, with a temperature sensor, a pressure sensor, and a vibronic sensor for determining a viscosity measurement value and, optionally, a density measurement value of the flowing gas mixture; and
  an evaluation unit for carrying out calculating steps according to the method, in particular, for calculating properties of the flowing gas mixture, in particular, the methane index.

In one embodiment of the invention, the vibronic sensor is a MEMS sensor, which has at least one oscillatable measuring tube through which a flow is possible and/or at least one oscillator surrounded by the flowing gas mixture, in particular, in the form of at least one oscillatable cantilever beam or an oscillatable tuning fork.

In one embodiment of the invention, the device furthermore comprises a thermal conductivity sensor.

BRIEF DESCRIPTION OF THE DRAWING

The invention is explained in the following in further detail on the basis of the exemplary embodiments shown in the figures. Shown are.

DETAILED DESCRIPTION

Figure 1:
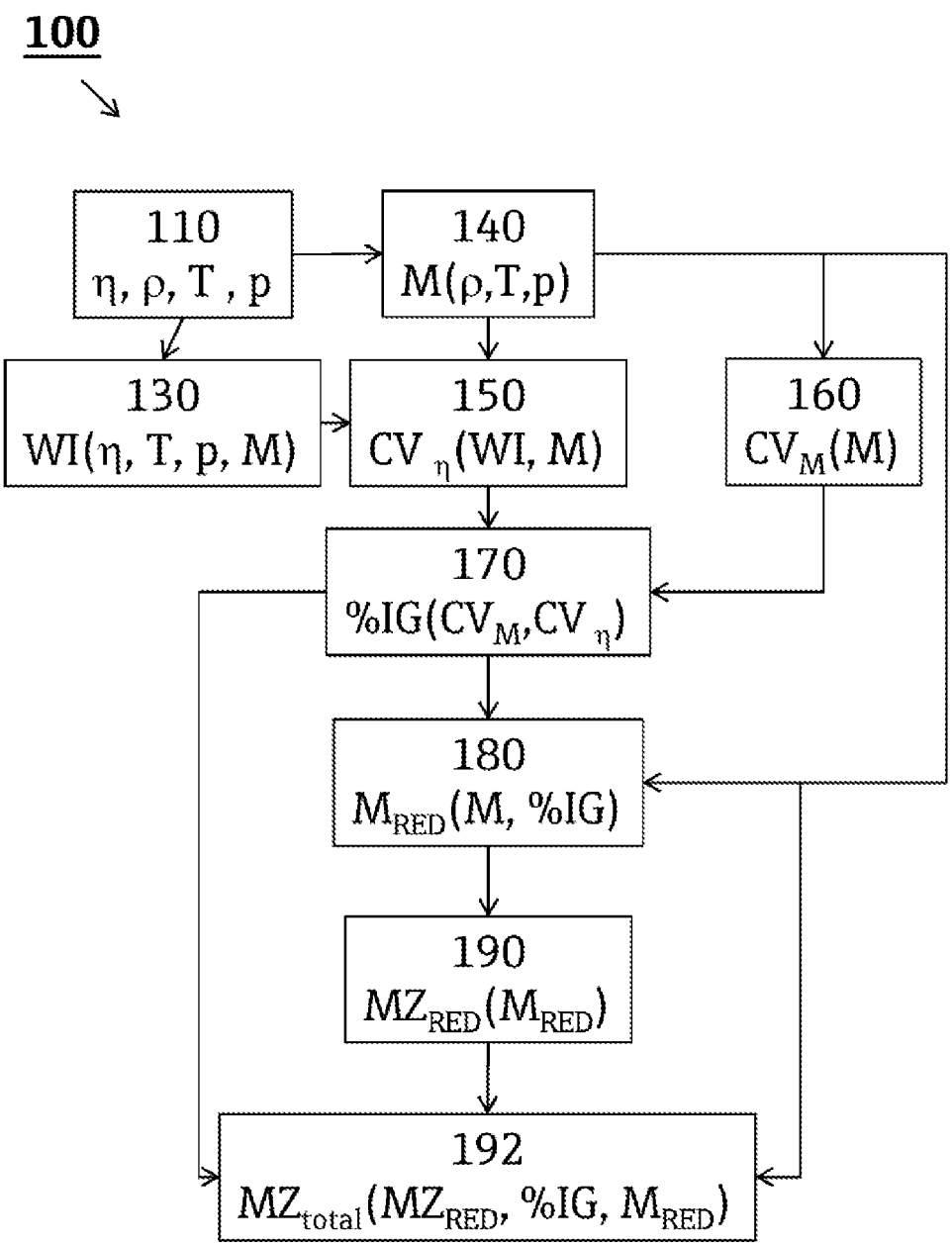
FIG. 1 shows a flow chart for a first exemplary embodiment of the method according to the present disclosure.

The first exemplary embodiment of the method according to the invention shown in FIG. 1 is suitable, in particular, for combustion gas mixtures containing only small amounts of hydrogen. In a step 110, the method 100 comprises detecting a viscosity measurement value $\eta$, a density measurement value $\rho$, a temperature measurement value T, and a pressure measurement value p of the flowing combustion gas mixture, wherein said measurement values are to be detected as simultaneously as possible, and the sensors required to do so are preferably arranged as closely together as possible, so that the measurement values form a value tuple of the gas mixture in a thermodynamic state. The viscosity is measured, for example, with a vibronic sensor, in particular, an oscillating cantilever, which is surrounded by the gas mixture. Optionally, a viscosity measurement value can first be determined under standard conditions from the current viscosity measurement value at a given pressure p and a given temperature T. The density of the combustion gas mixture can likewise be determined with the vibronic sensor, since the resonant frequency thereof depends upon the density.

A suitable micromechanical vibronic sensor is described, for example, in the still unpublished German patent application DE 10 2016 124 910.6.

In a step 130, a first value for the Wobbe Index $WI(\eta, T, p)$ of the combustion gas mixture is determined on the basis of a viscosity measurement value, be it either the directly measured viscosity measurement value or a viscosity measurement value derived therefrom, wherein this first value for the Wobbe index is determined independently of the density of the combustion gas mixture.

However, it is advantageous to first determine a standard viscosity under standard conditions $\eta_{ref}$ from a current viscosity value $\eta(T,p)$ at a given pressure p and a given temperature T, wherein the Wobbe index is then calculated on the basis of the standard viscosity under standard conditions. The standard viscosity $\eta_{ref}$ is to be calculated from a current viscosity value, e.g., with a polynomial in $\eta$, p, and T, in particular:

$$\eta_{ref}=C_0+C_1\cdot\eta+C_2\cdot p+C_3\cdot T+C_4\cdot T^2$$

wherein the $C_i$ are constants.

The Wobbe index W for the residual gas mixture is then determined as a linear function of the standard viscosity, i.e., $$W=A\eta_{ref}+B,+C*M+D*\lambda_{ref}$$

wherein A and B, C, and D are constants.

In a step 140, the average molar mass M ($\rho$, T, p) of the combustion gas mixture is determined from the density measurement value and the associated pressure and temperature measurement values.

Determining the average molar mass M of the gas mixture in one embodiment of the invention comprises calculating the average molar mass as a function of the density, pressure, and temperature $$M=f(\rho,T,p)$$

for example, by means of a polynomial in $\rho$, p, and T, i.e., $$M=\Sigma B_i \cdot T^{ti} \cdot \rho^{ri} \cdot p^{vi},$$

wherein i=0 ... k is an index of the summands, and the $B_i$ are the coefficients thereof, and $t_i$, $r_i$, and $v_i$ are integer exponents.

For example:

$$M=B_0+B_1 \cdot \rho \cdot T/p+B_2 \cdot \rho^2 \cdot T/p+B_3 \cdot \rho^2/p+B_4 \cdot (\rho \cdot T/p)^2+B_5 \cdot p.$$

A first value $CV_\eta$ for the calorific value of the combustion gas mixture is ascertained in the next step 150 from the average molar mass M($\rho$, T, p) and the viscosity-dependent first value for the Wobbe index.

$$CV_\eta = C^* W \cdot (M/M_{air})^{1/2}$$

Furthermore, in the next step 160, a second value for the calorific value of the combustion gas mixture is ascertained using only the average molar mass M($\rho$, T, p), which correlates with the calorific value as long as no inert gases are present:

$$CV_M = D_0 + M \cdot D_1,$$

wherein the $D_i$ are constants.

In the next step 170, the inert gas fraction % IG is determined from the deviation between the first value for the calorific value of the combustion gas mixture and the second value for the calorific value of the combustion gas mixture:

$$\% \; IG = E \cdot (CV_M/CV_\eta - 1),$$

wherein E is a constant.

In a subsequent step 180, the average molar mass $M_{RED}$ (M, % IG) of the combustion gas mixture reduced by the inert gas fraction, which essentially consists of hydrocarbon compounds, is ascertained on the basis of the inert gas fraction % IG and the average molar mass M of the combustion gas mixture:

$$M_{RED} = (M - \% \; IG \cdot M_{IG})/(1 - \% \; IG),$$

wherein $M_{IG}$ is the average molar mass of the inert gas. Depending upon the expected value for the mixing ratio between nitrogen and carbon dioxide, this results in values between 28 and 44, wherein values between 30 and 34, and, in particular, between 30 and 32, appear particularly suitable.

Under this assumption, in a following step 190, the methane index $MZ_{RED}(M_{RED})$ for a hydrocarbon mixture of the average molar mass $M_{RED}$ can be ascertained from the average molar mass $M_{RED}$ of combustion gas mixture reduced by the inert gas fraction—for example, according to:

$$MZ_{RED} = A + B \cdot M_{RED} + C \cdot M_{RED}^2,$$

wherein A, B, C are constants.

In a final step 192, the methane index $MZ_{RED}$ for the pure hydrocarbon mixture is corrected by the influence of the inert gases on the methane index in order to obtain the methane index $MZ_{total}$ for the flowing combustion gas mixture—for example, according to:

$$MZ_{total} = MZ_{RED} \cdot (A + B \cdot \% \; IG + C \cdot M_{RED}),$$

wherein A, B, C are constants.

Figure 2:
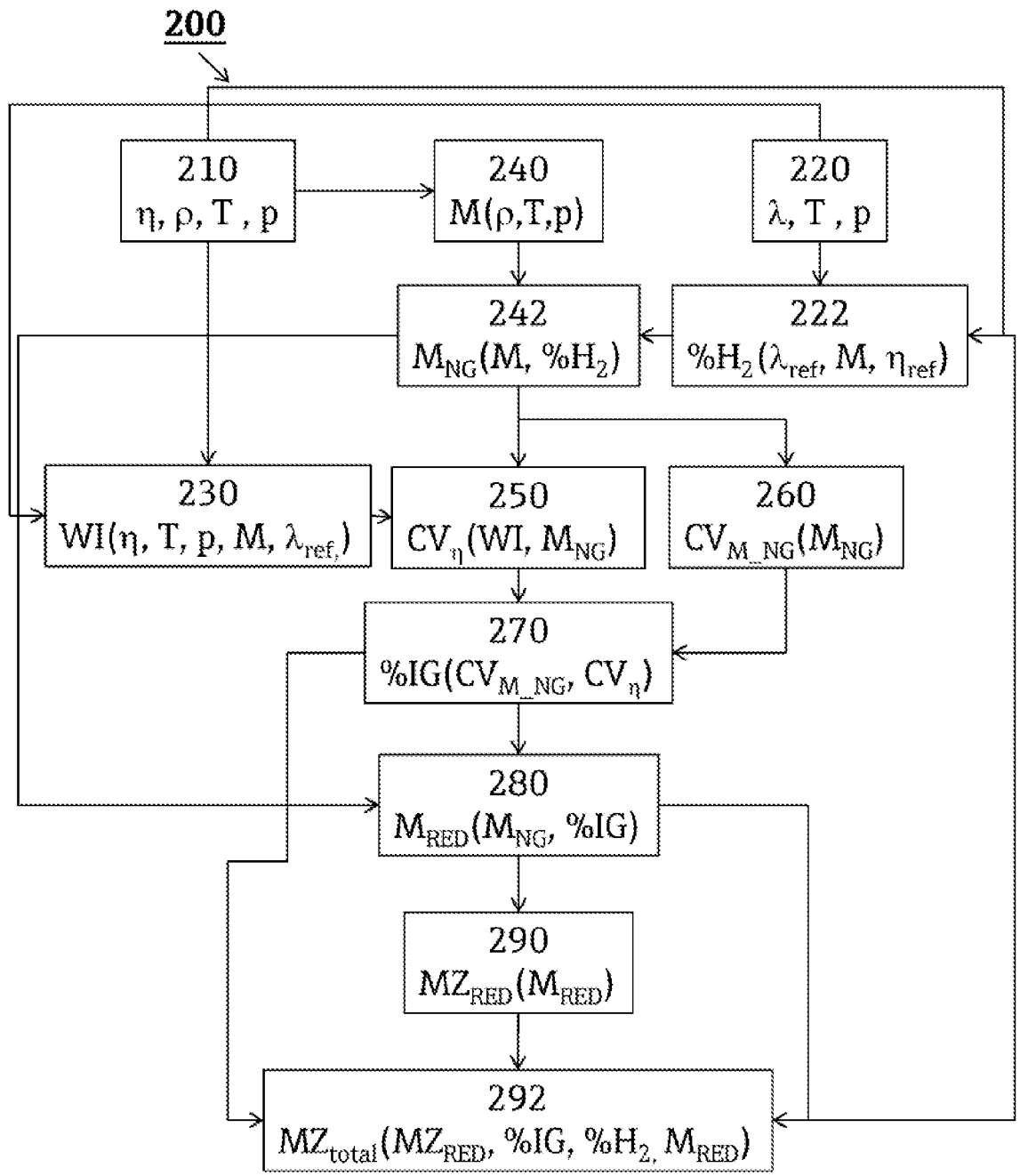
FIG. 2 shows a flow chart for a second exemplary embodiment of the method according to the present disclosure.
Figure 3:
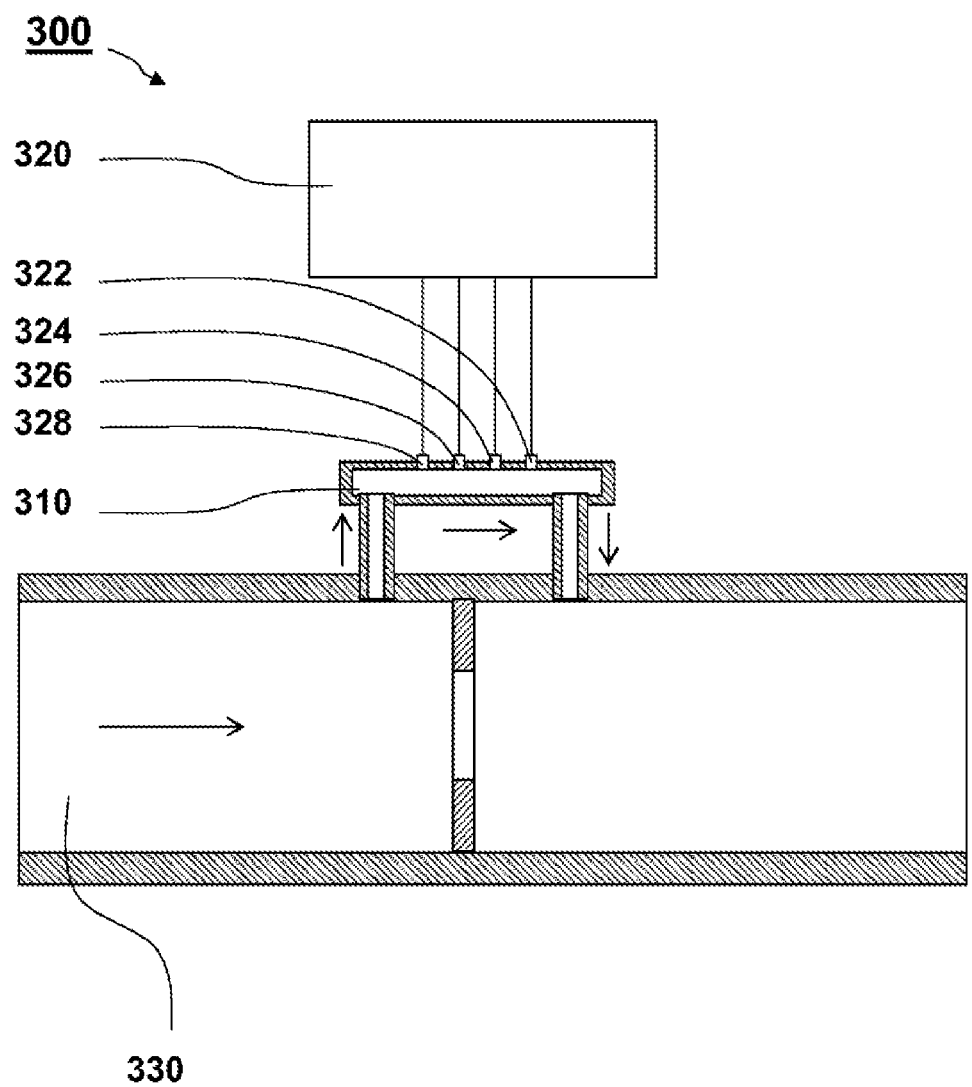
FIG. 3 shows a schematic illustration of an exemplary embodiment of a device according to the present disclosure for determining the methane index.

The second exemplary embodiment of the method according to the invention shown in FIG. 2 is modified compared to the first exemplary embodiment in order to also be able to analyze hydrogen-containing combustion gas mixtures. As before, the method 200 in a step 210 comprises detecting a viscosity measurement value $\eta$, a density measurement value $\rho$, a temperature measurement value T, and a pressure measurement value p of the flowing combustion gas mixture. The details explained in connection with the first exemplary embodiment apply here accordingly.

In an additional step 220, a measurement value for the thermal conductivity $\lambda$ and the associated pressure p and temperature measurement values T are detected, so as to ascertain the hydrogen fraction % $H_2$ in the combustion gas mixture on the basis of this value tuple, wherein, in particular, initially, a reference thermal conductivity $\lambda_{ref}$ under reference conditions is calculated from the thermal conductivity measurement value, based upon which the hydrogen fraction % $H_2$ is then determined.

The determination of the thermal conductivity value A at a given pressure and a given temperature is followed, in one embodiment of the invention, by a conversion into a standard thermal conductivity $\lambda_{ref}$ under standard conditions, e.g., with a polynomial in $\lambda$, p, and T, in particular, $$\lambda_{ref} = \Sigma A_i \cdot T^{ti} \cdot \lambda^{li} \cdot p^{vi}, M, \eta_{ref}$$

wherein i=0 ... k is an index of the summands, and the $A_i$ are the coefficients thereof, and $t_i$, $I_i$, and $v_i$ are integer exponents. For example:

$$\lambda_{ref} = A_0 + A_1 \cdot T + A_2 \cdot T^2 + A_3 \cdot p + A_4 \cdot \lambda + A_5 \cdot \lambda \cdot T + A_6^* \eta_{ref}$$

The hydrogen fraction is then determined according to:

$$\% \; H_2 = A \lambda_{ref} + B + C^* M + D^* \eta_{ref}$$

In a further step 230, a first value for the Wobbe index WI($\eta$, T, p) of the combustion gas mixture is determined on the basis of a viscosity measurement value, be it either the directly measured viscosity measurement value or a viscosity measurement value derived therefrom, wherein this first value for the Wobbe index is determined independently of the density of the combustion gas mixture.

In a step 240, the average molar mass M($\rho$, T, p) of the combustion gas mixture is determined from the density measurement value and the associated pressure and temperature measurement values. From the average molar mass of the combustion gas mixture M($\rho$, T, p) and the hydrogen fraction thereof, in a next step, the average molar mass $M_{NG}$ (M, % $H_2$) of a gas mixture adjusted for the hydrogen fraction is calculated.

A first value $CV_\eta$ for the calorific value of the gas mixture adjusted for the hydrogen fraction is ascertained in the next step 250 from the average molar mass $M_{NG}$ of the gas mixture adjusted for the hydrogen fraction and the viscosity-dependent first value for the Wobbe index.

Furthermore, in the next step 260, a second value $C_{VM\_NG}$ ($M_{NG}$) for the calorific value of the gas mixture adjusted for the hydrogen fraction is ascertained using only the average molar mass $M_{NG}$ of the gas mixture adjusted for the hydrogen fraction.

In the next step 270, the inert gas fraction % IG is determined from the deviation between the first value for the calorific value of the gas mixture adjusted for the hydrogen fraction and the second value for the calorific value of the gas mixture adjusted for the hydrogen fraction.

On the basis of the inert gas fraction % IG and the average molar mass $M_{NG}$ of the gas mixture adjusted for the hydrogen fraction, in a subsequent step 280, the average molar mass $M_{RED}(M_{NG}, \% IG)$ of the gas mixture, which essentially consists of hydrocarbon compounds, adjusted for the hydrogen fraction and for the inert gas fraction is ascertained. Under this assumption, in a following step 290, the methane index $MZ_{RED}(M_{RED})$ for a hydrocarbon mixture of the average molar mass $M_{RED}$ can be ascertained from the average molar mass $M_{RED}$ of the gas mixture adjusted for the hydrogen fraction and for the inert gas fraction.

In a final step 292, the methane index $MZ_{RED}$ for the pure hydrocarbon mixture is corrected by the influence of the inert gases and the hydrogen on the methane index in order to obtain the methane index $MZ_{total}$ for the flowing combustion gas mixture.

The exemplary embodiment of a device 300 according to the invention for carrying out the method according to the invention comprises a measuring cell 310 through which the gas mixture can flow and in which here are arranged only schematically illustrated sensor elements, viz., a cantilever oscillator 322 for determining the viscosity and the density of a gas mixture in the measuring cell, a pressure sensor 324, a temperature sensor 326, and a thermal conductivity sensor 328. The sensor elements are preferably implemented using microelectromechanical systems (MEMS) technology. The individual sensor principles are known per se to the person skilled in the art and need not be explained in more detail here. The device furthermore comprises an operating and evaluating unit 320 for driving the sensor elements, for evaluating the signals thereof, in order to determine the primary measurement variables, such as viscosity, pressure, temperature, thermal conductivity and density, and for ascertaining the methane index and auxiliary variables required for ascertaining the methane index, e.g., the average molar mass, the hydrogen fraction, the Wobbe index and/or the calorific value and/or the inert gas fraction of a gas mixture flowing through the measuring cell 310. For this purpose, the operating and evaluating unit comprises a processing unit, which can have a compact or modular design and can, in particular, comprise modules spatially separated from one another. The measuring cell 310 is connected to a gas line 330, in particular, in a bypass assembly, wherein a volume flow of the gas mixture can be driven across the measuring cell 310 by means of a pressure difference, e.g., as a result of a diaphragm or a Venturi nozzle in the pipeline, or through the measuring cell 310 by means of a pump, which is not shown here.

The invention claimed is:

1. A method for determining a methane index of a hydrocarbon-containing combustion gas mixture, the method comprising:
    flowing a combustion gas mixture through a measuring assembly;
    determining a viscosity value of the flowing combustion gas mixture;
    determining a density value or a sound velocity value of the flowing combustion gas mixture;
    determining a corresponding temperature value and a corresponding pressure value of the flowing combustion gas mixture;
    determining a value for an average molar mass of hydrocarbons contained in the combustion gas mixture as a function of at least the viscosity value and the density value or the sound velocity value, the determining comprising:
        ascertaining a value for the average molar mass of the flowing combustion gas mixture as a function of the density value or sound velocity value of the flowing combustion gas mixture;
        ascertaining a fraction of at least one foreign component in the combustion gas mixture, wherein the foreign component is free of hydrocarbon compounds; and
        ascertaining the value for the average molar mass of hydrocarbon compounds contained in the combustion gas mixture as the average molar mass of the combustion gas mixture adjusted for the at least one foreign component as a function of the ascertained value for the average molar mass of the combustion gas mixture and the fraction of the at least one foreign component in the combustion gas mixture,
    wherein the at least one foreign component includes an inert gas, and the fraction of the at least one foreign component in the combustion gas mixture defines an inert gas fraction, wherein the ascertaining of the inert gas fraction of the combustion gas mixture comprises:
        determining a first value of a variable representing an energy content of the combustion gas mixture as a function of the viscosity value;
        determining a second value of the variable representing the energy content of the combustion gas mixture as a function of the density value or sound velocity value of the combustion gas mixture and independently of the viscosity value; and
        determining the inert gas fraction of the combustion gas mixture as a function of a deviation between the first value and the second value of the variable representing the energy content of the combustion gas mixture; and
    determining the methane index as a function of the value for the average molar mass of hydrocarbon compounds contained in the combustion gas mixture.

2. The method of claim 1, wherein the hydrocarbon-containing combustion gas mixture includes natural gas or biogas.

3. The method of claim 1, wherein the at least one foreign component further includes carbon dioxide or nitrogen or both.

4. The method of claim 1, wherein the second value of the variable representing the energy content is a Wobbe index or a calorific value of the combustion gas mixture.

5. The method of claim 1, wherein the at least one foreign component further includes molecular hydrogen contained in the combustion gas mixture.

6. The method of claim 5, wherein the fraction of the at least one foreign component includes a fraction of the molecular hydrogen determined based on a thermal conductivity of the combustion gas mixture.

7. The method of claim 5, wherein:
    the average molar mass of the combustion gas mixture adjusted for the molecular hydrogen is determined as a function of the ascertained value for the average molar mass of the combustion gas mixture and the fraction of the molecular hydrogen in the combustion gas mixture;
    the inert gas fraction in the combustion gas mixture adjusted for the molecular hydrogen is determined;
    the average molar mass of hydrocarbon compounds contained in the combustion gas mixture as a function of the average molar mass of the combustion gas mixture adjusted for the molecular hydrogen is determined as a function of the ascertained value for the average molar mass of the combustion gas mixture adjusted for the molecular hydrogen and the inert gas fraction in the combustion gas mixture adjusted for the molecular hydrogen; and the methane index of hydrocarbon compounds contained in the combustion gas mixture is determined based on the ascertained value for the average molar mass of the hydrocarbon compounds contained in the combustion gas mixture.

8. The method of claim 7, wherein the methane index of the combustion gas mixture is determined based on the ascertained value for the methane index of the hydrocarbon compounds contained in the combustion gas mixture.

9. An apparatus for determining at least a methane index of a hydrocarbon-containing gas mixture, the apparatus comprising:
 a measuring assembly adapted to enable the gas mixture to flow therethrough, the measuring assembly including:
  a temperature sensor;
  a pressure sensor; and
  a vibronic sensor configured for determining a viscosity value and a density value of the gas mixture flowing through the measuring assembly; and
 an evaluation unit configured to calculate properties of the flowing gas mixture by at least:
  determining the viscosity value of the gas mixture using the vibronic sensor;
  determining the density value or a sound velocity value of the gas mixture using the vibronic sensor;
  determining a corresponding temperature value and a corresponding pressure value of the gas mixture using the temperature sensor and pressure sensor, respectively;
  determining a value for an average molar mass of hydrocarbons contained in the gas mixture as a function of at least the viscosity value and the density value or the sound velocity value, wherein the evaluation unit is further configured to:
   ascertain a value for the average molar mass of the gas mixture as a function of the density value or sound velocity value of the gas mixture;
   ascertain a fraction of at least one foreign component in the gas mixture, wherein the foreign component is free of hydrocarbon compounds; and
   ascertain the value for the average molar mass of hydrocarbon compounds contained in the gas mixture as the average molar mass of the gas mixture adjusted for the at least one foreign component as a function of the ascertained value for the average molar mass of the gas mixture and the fraction of the at least one foreign component in the gas mixture, wherein the at least one foreign component includes an inert gas contained in the gas mixture, wherein the fraction of the at least one foreign component in the gas mixture defines an inert gas fraction, and wherein the evaluation unit is further configured to:
  determine a first value of a variable representing an energy content of the gas mixture as a function of the viscosity value;
  determine a second value of the variable representing the energy content of the gas mixture as a function of the density value or sound velocity value of the gas mixture and independently of the viscosity value; and
  determine the inert gas fraction of the gas mixture as a function of a deviation between the first value and the second value of the variable representing the energy content of the gas mixture; and
 determining the methane index as a function of the value for the average molar mass of hydrocarbon compounds contained in the gas mixture.

10. The apparatus of claim 9, wherein the vibronic sensor is a microelectromechanical systems (MEMS) sensor having at least one oscillatable measuring tube through which the gas mixture can flow and/or at least one oscillatable cantilever beam or an oscillatable tuning fork surrounded by the gas mixture.

11. The apparatus of claim 9, wherein the at least one foreign component includes molecular hydrogen contained in the gas mixture, and wherein the evaluation unit is further configured to:
 determine the average molar mass of the gas mixture adjusted for the molecular hydrogen as a function of the ascertained value for the average molar mass of the gas mixture and the fraction of the molecular hydrogen in the gas mixture;
 determine an inert gas fraction in the gas mixture adjusted for the molecular hydrogen;
 determine the average molar mass of hydrocarbon compounds contained in the gas mixture as a function of the average molar mass of the gas mixture adjusted for the molecular hydrogen as a function of the ascertained value for the average molar mass of the gas mixture adjusted for the molecular hydrogen and the inert gas fraction in the gas mixture adjusted for the molecular hydrogen; and
 determine the methane index of hydrocarbon compounds contained in the gas mixture based on the ascertained value for the average molar mass of the hydrocarbon compounds contained in the gas mixture.

12. The apparatus of claim 9, further comprising a thermal conductivity sensor, wherein the fraction of the at least one foreign component is a fraction of the molecular hydrogen, and wherein the evaluation unit is further configured to:
 determine the fraction of the at least one foreign component based on a thermal conductivity of the gas mixture.

* * * * *